United States Patent [19]

Belica et al.

[11] Patent Number: 4,900,828
[45] Date of Patent: Feb. 13, 1990

[54] INTERMEDIATE COMPOUNDS AND AN IMPROVED PROCEDURE FOR THE SYNTHESIS OF 2',3'-DIDEOXYCYTIDINE

[75] Inventors: Peter S. Belica, Wanaque; Tai-Nang Huang, Westfield; Percy S. Manchand, Montclair, all of N.J.; John J. Partridge, Chapel Hill, N.C.; Steve Tam, West Caldwell, N.J.

[73] Assignee: Hoffmann-LaRoche Inc., Nutley, N.J.

[21] Appl. No.: 192,978

[22] Filed: May 12, 1988

[51] Int. Cl.$^4$ ............................................ C07D 239/02
[52] U.S. Cl. ........................................................ 544/317
[58] Field of Search .......................................... 544/317

[56] References Cited

U.S. PATENT DOCUMENTS 4,604,382  1/1983  Lin et al. .............................. 544/317

OTHER PUBLICATIONS

Adachi et al., *Journal of Organic Chemistry*, 44:9, 1404 (1979).
*Tetrahedron Letters*, 29, 11:1239 (1988).
Ashe et al., *The Journal of Organic Chemistry*, 44(9):1409 (1979).
Lin et al., *The Journal of Medicinal Chemistry*, 21(1):106 (1978).
Lin et al., *The Journal of Medicinal Chemistry*, 26(4):544 (1983).
Kranitsky et al., *Journal of Medicinal Chemistry*, 26(6):891 (1983).
Lin et al., *The Journal of Medicinal Chemistry*, 26(12):1691.
Samukov et al., *Chemical Abstracts*, 98:161094x (1983).
Marumoto et al., *Chem. Pharm. Bulletin*, 22(2):342 (1974).
Horowitz et al., *Journal of Organic Chemistry*, 32:817 (1967).
Prisbee et al., *Synthetic Communications*, 15(5):401 (1985).
Corey et al., *Tetrahedron Letters*, 23(19):1979 (1982).
Schroeder et al., *Journal of Medicinal Chemistry*, 24(9):1078 (1981).
Niedballa et al., *Journal of Organic Chemistry*, 39(25):3654 (1974).
Vorbruggen et al., *Chem. Ber.*, 114:1234 (1981).
Fleet et al., *Tetrahedron Letters*, 28(31):3615 (1987).

*Primary Examiner*—Mary C. Lee
*Assistant Examiner*—J. Richter
*Attorney, Agent, or Firm*—George M. Gould; William H. Epstein; Julie M. Prlina

[57] ABSTRACT

A method for the synthesis of 2',3'-dideoxycytidine comprising a novel procedure of bromoacetylating cytidine to yield novel intermediates which are subsequently reduced and hydrogenated by novel procedures to yield 2',3'-dideoxycytidine.

21 Claims, No Drawings

INTERMEDIATE COMPOUNDS AND AN IMPROVED PROCEDURE FOR THE SYNTHESIS OF 2',3'-DIDEOXYCYTIDINE

BACKGROUND OF THE INVENTION

It is known that the 2',3'-dideoxy analogs of the common nucleosides are effective in protecting $T_4^+$ lymphocytes against the cytopathic effects of various viruses, including HIV (human immunodeficiency virus). In the quest to find cures for viral diseases, particularly AIDS, it is desirable to simplify and economize high yield synthetic procedures for the 2',3'-dideoxynucleosides such as 2',3'-dideoxycytidine (ddC).

The art is replete with various synthetic methods for 2',3'-dideoxynucleosides, most of which are costly, low yield procedures requiring extensive manipulations. For example, 2',3'-dideoxycytidine (ddC) was first prepared in 1967 and is currently undergoing clinical trials because it appears to be the most potent anti-AIDS therapeutic to date. Six published syntheses of ddC are available, three of which use 2'-deoxycytidine as the starting material. (See Horowitz, et al., *J. Org. Chem*, 32, 817 (1967); Samukov, et al., *Bioorg. Khim.*, 9, 132 (1983) or Chemical Abstracts, 98, 161094X, (1983); Prisbe et al., *Syn. Commun.*, 15, 401 (1985); and Marumoto et al., *Chem. Pharm. Bull.*, 22, 123 (1974)); Kawana et al., *Chem. Letts.*, 2419 (1987); Farina et al., *Tetrahedron Letters*, 29, 1239 (1988).

In the synthesis of ddC the current procedures exhibit numerous disadvantages such as requiring expensive and not easily accessible starting materials, extensive manipulation including chromatography, as well as resulting in a low overall yield.

For example, one synthetic scheme for ddC involves a bromoacetylation procedure where N-protected cytidine is reacted with acetyl bromide to yield bromoacetylated intermediate compounds which are further reduced and hydrogenated to ddC. This particular procedure results in a low overall yield due largely to the poor yield of the intermediate compounds after the bromoacetylation step.

Other hydrogenation and reduction steps also used in the current procedures do not result in optimal yields of intermediate and hence final products.

Therefore, there is a need for a simple, economic, high yield synthetic procedure for the manufacture of 2',3'-dideoxycytidine.

Definitions 1. bromoacetylation procedure—means a procedure for the synthesis of 2',3' dideoxycytidine wherein bromoacetylation the cytidine derivatives comprising one of the intermediate steps.

2. bromoacetate derivative—means a product of cytidine derivatives which have been bromoacetylated into a 2'-bromo-3'-acetyldideoxycytidine or a 2'-acetyl-3'-bromodideoxycytidine.

3. zinc/copper couple—means a combination of zinc and copper prepared according to the method set forth in Example 5.

4. THF—means tetrahydrofuran
5. MeOH—means methanol
6. regioisomer—means positional isomers such that two positions on the compound are equivalent, for example: when bromoacetylating N-acetylcytidine two compounds which are regioisomers of one another at the 2' and 3' positions result.

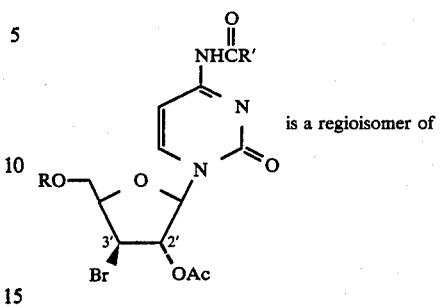 is a regioisomer of

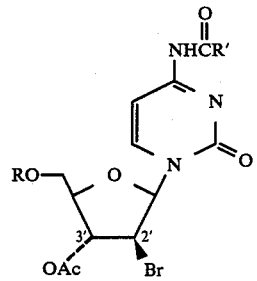

7. Compound—when used in the context of the instant specification and claims this term will include the regioisomers of the compound where possible.

8. Ac—means acetyl

9.

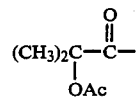

means 2-acetoxy-2-methylpropanoyl 10. protecting group—means any chemical group of radical which is used to block any undesired side reactions at potentially reactive sites on any chemical compound during synthetic procedures. For example the t-butyldimethylsilyl group is one known protecting group for the 5' hydroxy position of nucleosides, and acyl, aroyl, or substituted aroyl groups, for example, are known protecting groups for the 4-amino positions of nucleosides.

11. lower alkyl—means a straight or branched chain hydrocarbon containing from 1 to 7 carbon atoms.

12. aryl—means substituted or unsubstituted phenyl with the substituents selected from the groups consisting of lower alkyl, lower alkoxy, nitro, amine, or halogen.

13. lower alkoxy—means a lower alkyl ether group where the alkyl is as defined herein.

14. halogen—means chlorine, fluorine, bromine, or iodine.

15. aralkyl—means an alkyl side chain substituted with one or more aryl groups.

16. 2',3'-didehydro derivative—means a derivative of 2',3'-dideoxycytidine wherein there is a double bond between the 2' and 3' carbons.

SUMMARY OF THE INVENTION

The instant invention is related to the synthesis of 2',3'-dideoxycytidine (ddC) and comprises:

(a) a novel bromoacetylation step in the synthesis of ddC according to Scheme I.

(b) a novel reductive elimination step in the synthesis of ddC according to Scheme I.

(c) a novel hydrogenation step in the synthesis of ddC according to Scheme I.

The instant invention also comprises the novel intermediate compounds which result from the synthesis of ddC according to Scheme I, as well as the method by which these novel intermediates are synthesized.

DETAILED DESCRIPTION

The instant invention first comprises novel intermediate compounds in the synthesis of ddC according to Scheme I. First is a compound of the formula

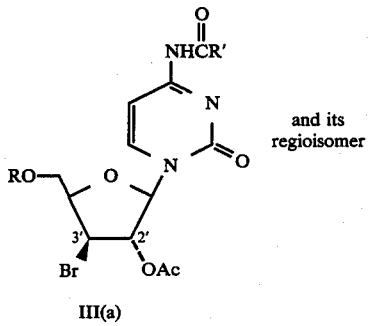

and its regioisomer

III(a)

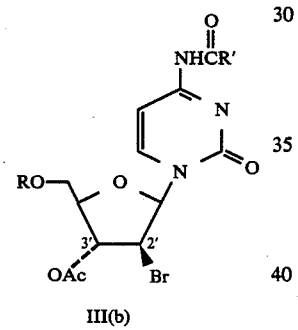

III(b)

wherein R' is substituted or unsubstituted lower alkyl, aryl, or aralkyl with the substituents selected from the group consisting of halogen, alkyl, nitro, or alkoxy; and R is substituted or unsubstituted 2-acetoxy-2-methylpropanoyl, 2-acetoxypropanoyl, or 2-acetoxybenzoyl.

If the 2-acetoxy-2-methylpropanoyl, 2-acetoxypropanoyl, or 2-acetoxybenzoyl is substituted, the possible substituents may be selected from the group consisting of lower alkyl, aryl or aralkyl.

Preferred is where R' is $CH_3$ and where R is unsubstituted 2-acetoxy-2-methylpropanoyl, 2-acetoxypropanoyl, or 2-acetoxybenzoyl.

The invention also comprises compounds of the formula

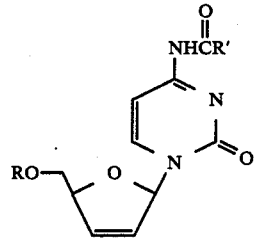

IV wherein R' and R are as in Formula III.

Preferred is the Formula IV compound where R' is $CH_3$ and R is unsubstituted 2-acetoxy-2-methylpropanoyl, 2-acetoxypropanoyl, or 2-acetoxybenzoyl.

The instant invention also comprises compounds of the formula

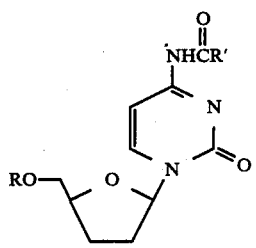

V wherein R' and R are as in Formula IV.

Preferred is the Formula V compound where R' is $CH_3$ and R is unsubstituted 2-acetoxy-2-methylpropanoyl, 2-acetoxypropanoyl, 2-acetoxybenzoyl.

These compounds are novel intermediates in the synthesis of ddC according to Scheme I.

Scheme I

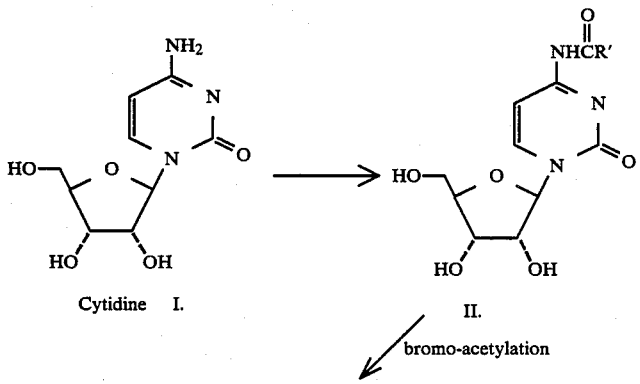

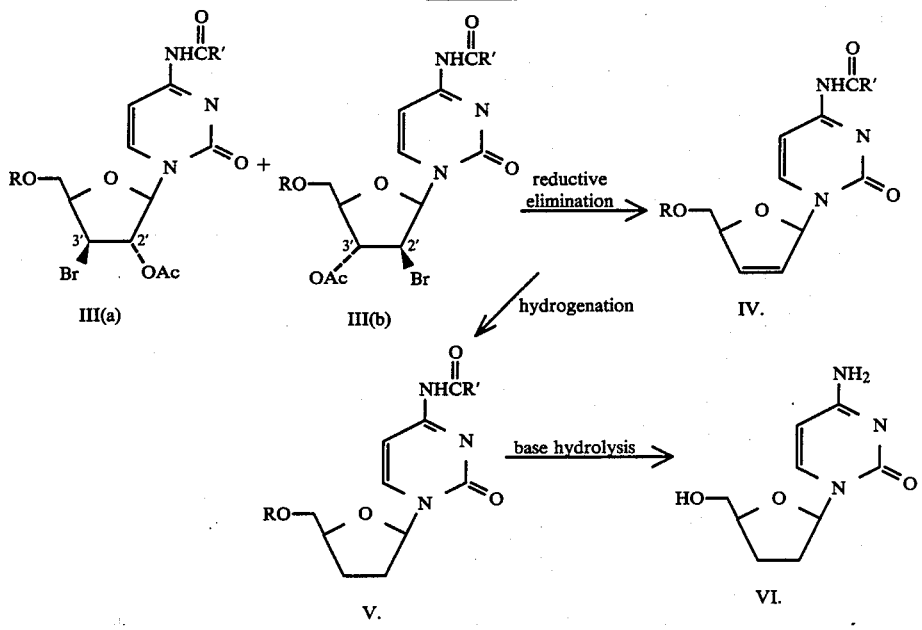

Scheme I

In Scheme I, the 4-amino position of cytidine is first protected with a suitable protecting group by methods known in the art. For example the reaction of cytidine with acetic anhydride according to known methods yields N-acetyl cytidine.

The instant invention also comprises a novel bromoacetylation step in the synthesis of ddC according to Scheme I. This novel step comprising two different embodiments, yields the compounds of Formula III.

In the first embodiment, the N-acetyl protected cytidine is reacted with a reagent selected from the group consisting of substituted or unsubstituted 2-acetoxy-2-methylpropanoyl bromide, 2-acetoxybenzoyl bromide, 2-acetoxypropanoyl bromide where the possible substituents are as set forth in Formula III.

Preferred in this embodiment is where the N-acetylcytine is reacted with unsubstituted 2-acetoxy-2-methylpropanoyl bromide, or 2-acetoxypropanoyl bromide. Examples 2, 3, and 4 illustrate the bromoacetylation of N-acetylcytidine with each of these reagents.

In the second embodiment the N-acetylcytidine is treated with HBr in acetic acid as set forth in Example I. The bromoacetylation of N-acetylcytidine according to either of the above embodiments results in a mixture of bromoacetates in high yield.

The instant invention also comprises a novel reductive elimination step in the synthesis of ddC according to Scheme I to yield the Formula IV compound. This novel step is comprises of two embodiments. First, the Formula III compound is reduced over a zinc-copper couple to yield the Formula IV compound. (See Examples 5 and 6). The Formula IV compound may also be obtained by utilizing an electrolytic cell as set forth in Example 11.

The instant invention also comprises a novel hydrogenation step in the synthesis of ddC according to Scheme I to yield the formula V compound. The Formula IV compound is hydrogenated over a palladium on carbon catalyst with solvent mixtures containing THF. The solvent mixture contains particularly methanol and THF.

ddC is then obtained by removing the 4-amino and 5' hydroxy blocking groups according to base hydrolysis methods.

The present invention will be described in connection with the following examples which are set forth for the purpose of illustration only.

EXAMPLE 1

Preparation of N-Acetyl 3'-Bromo-3'-deoxycytidine-2'-, 5'-diacetate

A 250 mL round-bottomed flask equipped with a magnetic stirring bar, a condenser, and a drying tube was charged with 5 g of N-acetylcytidine and 50 mL 30% hydrogen bromide in acetic acid and 5 mL acetic anhydride (Fisher) and heated in an oil bath at 50° for 18 hours. This reaction was cooled to room temperature and dissolved in 250 mL of methylene chloride (Fisher) and washed 2 times with 250 ml of 0.05M potassium phosphate buffer pH7 (Fisher) and 2 times with 250 mL of saturated aqueous sodium bicarbonate (Fisher). The aqueous layers were washed with 250 mL of methylene chloride. The two organic layers were combined and dried over anhydrous sodium sulfate and evaporated to dryness to yield 6.1 g (81%) of a mixture of N-acetyl-3'-bromo-3'-deoxycytidine-2'-, 5'-diacetate also known as 4-(acetylamino)-1-(3'-bromo-2',5'-di-O-acetyl-β-D-xylofuranosyl)-2-(1H)-pyrimidinone and the 2',3' regioisomer thereof.

EXAMPLE 2

Bromoacetylation of N-acetylcytidine with 2Acetoxy-2-methylpropanoyl Bromide

A 5 L three-nicked, round-bottomed flask equipped with a mechanical stirrer, thermometer, nitrogen inlet tube, and additional funnel was charge with 142.6 g (0.5 mole) of N-acetylcytidine, and 1.25 L of acetonitrile. The suspension was stirred under nitrogen, cooled to 5° C. (ice-bath), and treated dropwise (during 20 min.)

with 225 ml of 2-acetoxy-2-methylpropanoyl bromide (AIBB) during 30 minutes. At the completion of the addition, a homogeneous solution resulted. It was stirred at room temperature overnight (the reaction was complete within 3 hr), cooled to 5° C., and diluted with 1.25 L of ethyl acetate. After recooling to 5° C., 2.0 L of saturated sodium bicarbonate was added. The mixture was stirred for 5 minutes, the organic phase was separated, and the aqueous phase was back-extracted with 500 mL of ethyl acetate. The combined organic extracts were washed with 1 L of saturated brine, dried (MgSO$_4$), and evaporated to give a gum. Final drying at 40° C. (1 mm) for 1 hr gave 264.7 g (102%) of a white solid. High pressure liquid chromatographic analysis gave the following results (major peaks only):

| Compound | Percent | Relative Retention Time RRT (min) |
|---|---|---|
| III(a)$_2$ | 55% | 48.77 |
| III(b)$_2$ | 30% | 60.20 |

Two byproducts where R=CH$_3$CO and R'=CH$_3$ are 9% (RRT=15.03 min) and 2% (RRT=18.53 min). HPLC conditions are methanol: water (40:60) with C$_{18}$ column and detection at 245 nm.

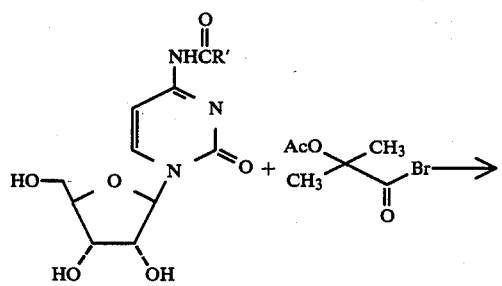

II

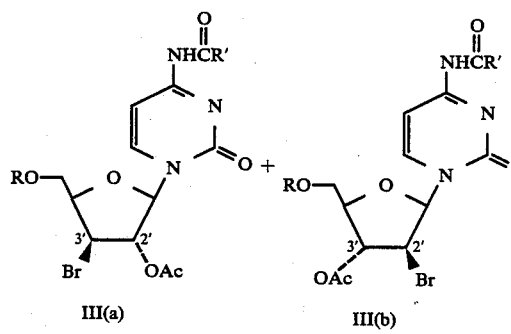

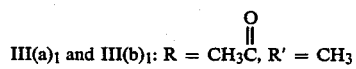

III(a)$_1$ and III(b)$_1$: R = CH$_3$C(=O), R' = CH$_3$

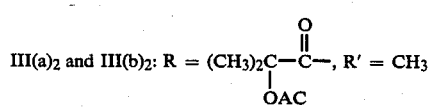

III(a)$_2$ and III(b)$_2$: R = (CH$_3$)$_2$C(OAc)—C(=O)—, R' = CH$_3$

An analytical sample of III(a) or III(b), was prepared by recrystallization from warm isopropyl alcohol, m.p. 182°–184°; [α]$_D^{25}$+41.5° (C 0.995, CHCl$_3$).

EXAMPLE 3

Preparation of [2R-[2 alpha, 3 beta, 4 alpha, 5 alpha (S*)]]-N-[1-[3-(Acetyloxy)-5-[(2-(acetyloxy)-1-oxo-propoxy] methyl]-4-bromotetrahydro-2-furanyl]-1,2-dihydro-2-oxo-4-pyrimidinyl]acetamide III(a) and its regioisomer III(b)

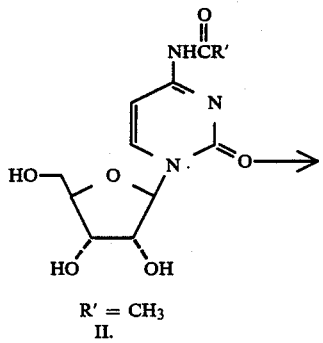

R' = CH$_3$
II.

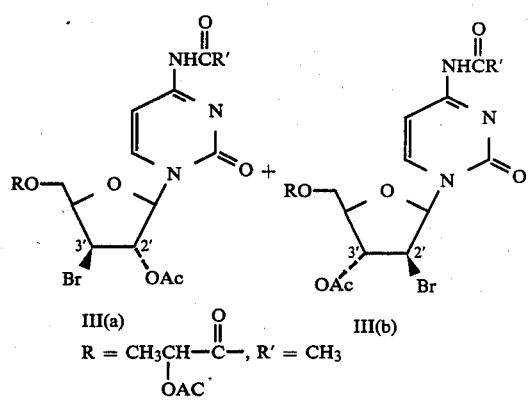

III(a)    III(b)

R = CH$_3$CH(OAc)—C(=O)—, R' = CH$_3$

A 1-L, three-necked, round-bottomed flask equipped with a mechanical stirrer and argon inlet was charged with 28.52 g of N-acetylcytidine in 250 mL of acetonitrile. The mixture was cooled to 10° C. and treated with 48.75 g of (S)(−)-2-acetoxypropionyl bromide during 15 minutes. It was stirred at room temperature overnight, cooled to 10° C., treated with 400 mL of cold (0° C.) saturated sodium bicarbonate, and extracted with 250 mL of ethyl acetate. The extract was washed with 200 mL of saturated brine, dried (MgSO$_4$) and evaporated to give 45.45 g of a white foam.

High pressure liquid chromatographic analysis gave the following results (major peaks only):

| Compound | Percent | Relative Retention Time of RRT (min) |
|---|---|---|
| III(a) | 40% | 28.53 |
| III(b) | 24% | 37.60 |

Reversed phase chromatography (C$_{18}$ column) with 40% methanol in water gaave a pure sample of III(a).

EXAMPLE 4

Preparation of
N-Acetyl-3-bromo-3'-deoxycytidine-2'-acetate-5'-[2(acetyloxy)benzoate]

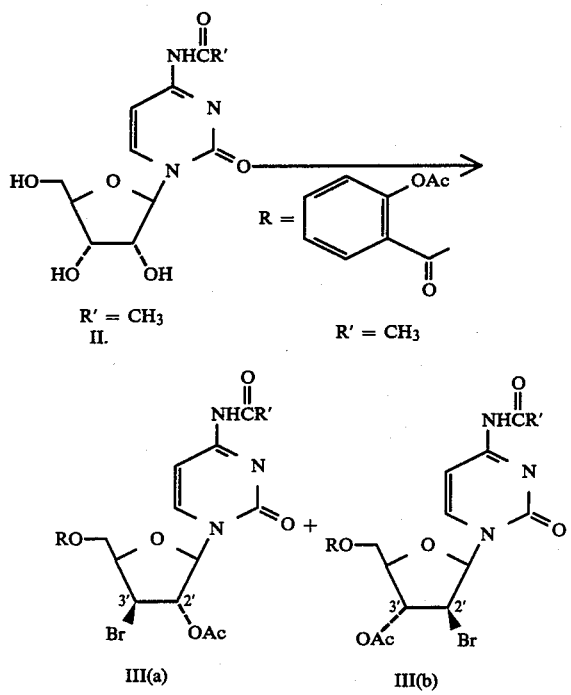

A 100-ml, 3-necked, round-bottomed flask was charged with 4.5 g of N-acetylcytidine in 45 mL of methylene chloride. The stirred mixture was cooled to 5° C. and treated with 11.5 g of 2-acetoxy-benzoyl bromide. Stirring was continued at room temperature for 4 h, and the mixture was diluted with 70 mL of sodium bicarbonate. The organic phase was separated and the aqueous phase was extracted with 50 mL of methylene chloride. The combined organic was washed with saturated brine, dried (MgSO$_4$), and evaporated to give 10.4 g of the Formula I compound wherein R is 2-acetoxybenzoyl as a foam. Chromatography of a 3.5 g portion of reversed phase chromatography (C$_{18}$ column) with 40% methanol in water gave 12.2 g of a mixture of bromoacetates III(a) and III(b) UV (EtOH):298 (E=9,600), 243 (E=20,000) and 217 (E=17,500) nm.

| Compound | Percent | Relative Retention Time of RRT (min) |
|---|---|---|
| III(a) | 29.6% | 53.60 |
| III(b) | 48.3% | 58.40 | which was crystallized from isopropyl alcohol, mp 186°-187° C.; UV 298 (E=7,310), 248 (E=15,030), and 211 (E=17,600) nm.

EXAMPLE 5

Preparation of Zinc-Copper Couple

A 12 L three-necked, round-bottomed flask equipped with a mechanical stirrer was charged with 4.50 kg of zinc dust (New Jersey Zinc Co.). The zinc dust was washed with 3.75 L of 3% aqueous hydrochloric acid by stirring for 3 to 5 minutes. The hydrochloric acid was decanted from the solid. This cycle was repeated with 3×3.75 L=14.0 L of 3% hydrochloric acid. The reaction was slightly exothermic and the volume of the zinc dust increased to double its original volume. The zinc dust was then washed with 4×3.0 L=12.0 L of deionized water to remove any residual hydrochloric acid. After all the water was decanted, the spongy zinc layer was treated with a solution made by dissolving 240.0 g of cupric sulfate dihydrate (Fisher) in 7.5 L of deionized water. The suspension was stirred rapidly as the solution was added. The aquamarine color of the cupric sulfate solution was removed almost immediately and the zinc suspension changed in color from gray to black. The near colorless aqueous layer was decanted and the solid was washed with 4×3.0 L=12.0 L of deionized water. The suspension of zinc-copper couple was filtered in a large sintered glass funnel through a piece of Whatman No. 1 filter paper, then washed successively with 4×30 L=12.0 L of 2B ethanol (Tank Farm) and 3×3.0 L=9.0 L of ether. The black solid was air-dried and transferred to a large glass tray. The solid was carefully dried at 25° and 140 mm overnight to remove ether, then for 3 hr at 130°-140° C. (0.5 mm). The solid was cooled to room temperature under vacuum and was stored under argon in amber bottles. The procedure yielded 3.84 kg of zinc-copper couple.

EXAMPLE 6

Treatment of
4-(Acetylamino)-1-(3'-deoxy-3'-bromo-2',5'-di-O-acetyl-β-D-xylofuranosyl)-2-(1H)-pyrimidinone with Zinc-Copper Couple: Preparation of N-Acetyl 2',3'-Didehydro-2',3'-dideoxycytidine 5'Acetate In two 12 L flasks were placed 1.26 kg of 4-(acetylamino)-1-(3'-deoxy-3'-bromo-2',5'-di-O-acetyl-β-D-xylofuranosyl)-2(1H)-pyrimidinone and its 2',3'-regioisomer which contained varying amounts of ethanol. To each flask was added 4.0 L of acetonitrile to dissolve the solids. The solutions were then individually evaporated to dryness on a rotary evaporator at 50° and 70 mm to remove the residual ethanol. Two 22 L three-necked, round-bottomed flasks equipped with mechanical stirrers, gas inlet tubes, and argon bubblers were each charged with ca. 1.26 kg of dry bromoacetate and 16.0 L of acetonitrile. After the solids had dissolved, 350.0 g of zinc-copper couple was added to each flask and the heterogeneous mixtures were degassed at 70 mm and layered with a nitrogen atmosphere. The mixture was degassed and relayered with nitrogen twice and a small volume of nitrogen was continuously bubbled into the mixture with a gas inlet tube that extended ½-1" below the surface. Failure to rigorously remove all oxygen from the mixture, lead to slow and incomplete reactions with low yields and partial deacetylation of the product. HPLC analysis of the reactions shows them to be complete after stirring overnight (16-18 hr) at room temperature. Each reaction was filtered through a 1" Celite pad on a sintered glass funnel to remove unreacted zinc-copper couple. The filter beds were washed with 2.0 L of acetonitrile. Then 250 mL of acetic anhydride, and 250 mL of pyridine were added to each reaction to reacetylate any deacetylated product. The reactions were immediately concentrated together in one large rotary evaporator at 50° (70 mm). The residue was suspended in 40.0 L of methylene chloride in a large extractor. This suspension was washed with a warm solution of 1.50 kg of sodium bicarbonate and 1.50 kg of disodium ethylenediamine tetracetate (disodium EDTA) previously dissolved in 15.0 L of deionized water by heating on a steam bath to 50° C. The buffered EDTA solution was added carefully since foaming sometimes was a problem. After the layers were separated, a fresh batch of 15.0 L of buffered EDTA solution was added to the aqueous layer and the aqueous layer extracted with 40.0 L of methylene chloride by stirring for 15 minutes. The organic layer was separated and the aqueous layer filtered to remove insoluble solids. These solids were suspended to 15.0 L of warm buffered EDTA solution and extracted with 40.0 L of methylene chloride with rapid stirring for 15 minutes. All of the organic layers were washed in succession with 2×15.0 L=30.0 L of warm buffered EDTA and 20.0 L of saturated sodium bicarbonate solution. The layers were separated and the organic layers were collected in six 20 L glass bottles. Each bottle was dried over anhydrous sodium sulfate containing 20 g of SG extra charcoal with stirring. The mixture was filtered through a 1" Celite pad and concentrated at 50° (70 mm) to leave a dark semisolid. This solid was triturated with 4.0 L of cold tetrahydrofuran (Fisher, HPLC grade) and 2.0 L of petroleum ether (Fisher). The tan solid was dried to constant weight to give 986.0 g of N-acetyl 2',3'-didehydro-2',3'-dideoxycytidine 5'-acetate. HPLC analysis showed this material to be 93% pure, but suitable for use in the next step. The 986.0 g of 93% pure material equaled 912.0 g (55%) of pure product. Yields in other reactions ranged from 45–55%. An analytical sample was prepared by recrystallization from tetrahydrofuran to yield white solid, m.p.>350°; $[\alpha]_D^{25}+15.8°$ (c=0.33, DMSO); lit. m.p.>280° [T. Adachi, T. Iwasaki, I. Inoue, and M. Miyoshi, *J. Org. Chem.*, 44, 1404 (1979)].

EXAMPLE 7

Preparation of a mixture of N-Acetyl 2,'3'-didehydro-2',3'-dideoxycytidine 5'-Acetate and N-Acetyl 2',3'-didehydro-2',3'-dideoxycytidine 5'-isobutrylacetate

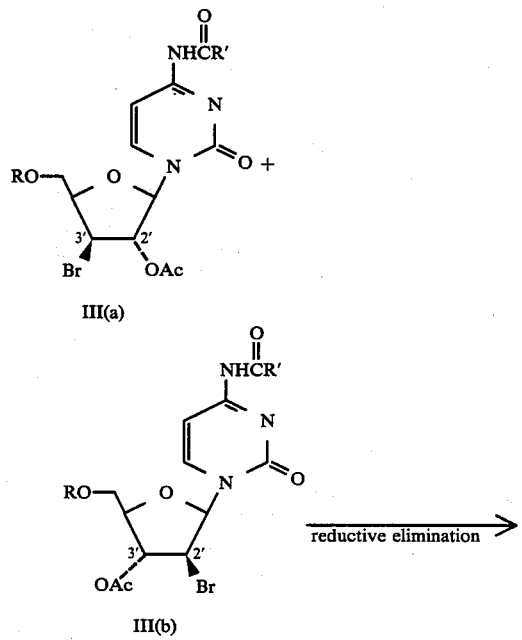

III(a)₁ and III(b)₁: R = CH₃C(=O), R' = CH₃

III(a)₂ and III(b)₂: R = (CH₃)₂C(OAc)—C(=O)—, R' = CH₃

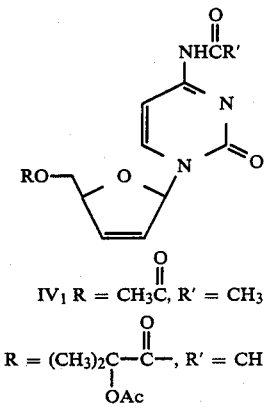

IV₁ R = CH₃C(=O), R' = CH₃

IV₂ R = (CH₃)₂C(OAc)—C(=O)—, R' = CH

A 5 L three-necked, round-bottomed flask equipped with a mechanical stirrer and nitrogen inlet was charged with 259.0 g of a mixture of bromoacetates from Example 2 in 2.5 L of acetonitrile. The mixture was deoxygenated by evacuation followed by filling the reaction vessel with argon (oxygen-free nitrogen may be used); this procedure was repeated three times. 100 g of zinc-copper couple (obtained as in Example 5) was added, and the mixture was stirred under argon at room temperature overnight. It was filtered over Celite, the flask was rinsed out with 200 mL of acetonitrile, and the rinse was used to wash the Celite. The combined filtrate and washing were evaporated (40° C.), and the residue was dissolved in 1.25 L of methylene chloride. This was added to a previously prepared solution of 200 g of ethylenediaminetetraacetic acid disodium salt dihydrate (Fluka) in 2.0 L of deionized water containing 200 g of sodium bicarbonate. The mixture was stirred vigorously for 1.5 hr, and filtered over Celite, which was washed with 300 mL of methylene chloride. The organic phase was separated and the aqueous phase was re-extracted with 500 ml of methylene chloride. The combined organic was washed with 250 mL of saturated sodium bicarbonate, which was back-extracted with 100 mL of methylene chloride. The combined organic was dried (MgSO₄), filtered, and concentrated to ca. 800 ml. To this was added 30 mL of acetic anhydride followed by 40 g of poly-4-vinylpyridine (Riley Tar), and the mixture was stirred under nitrogen for 3 hr. It was filtered over Celite, which was washed with 200 mL of methylene chloride. The combined filtrate and washing were evaporated, 250 mL of toluene was added, and the mixture was evaporated again. 500 mL of ether was added with vigorous stirring for 15 minutes. The mixture was filtered (some scraping of the flask was necessary) and washed with 200 mL of ether to give 143.3 g of a mixture of 5 and 6 as a tan-colored solid.

HPLC Analysis

| Compound | Percent | Relative Retention Time of RRT (min) |
|---|---|---|
| IV$_1$ R = CH$_3$C(O)—, R' = CH$_3$ | 6% | 5.83 |
| IV$_2$ R = (CH$_3$)$_2$—C(OAc)—C(O)—, R' = CH$_3$ | 91% | 13.50 |

Recrystallization of the mixture from hot tetrahydrofuran yielded pure N-acetyl 2',3'-didehydro-2',3'-dideoxycytidine 5'-isobutrylacetate, mp 173°–175°; $[\alpha]_D^{25}+123.5°$ (Cl.O, CHCl$_3$).

EXAMPLE 8

Preparation of [2R-[2 alpha, 5 alpha (S*)]]-N-[1-[5-[[2-(Acetyloxy)-1-oxopropoxy]methyl]-2-5-dihydro-2-furanyl]-1,2-dihydro-2-oxo-4-pyrimidinyl]acetamide

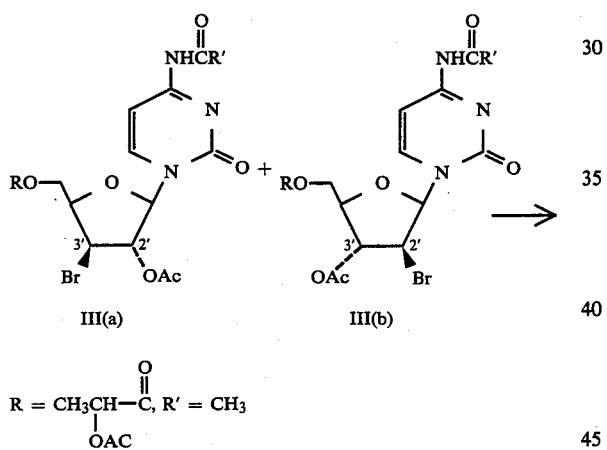

R = CH$_3$CH(OAC)—C(O)—, R' = CH$_3$

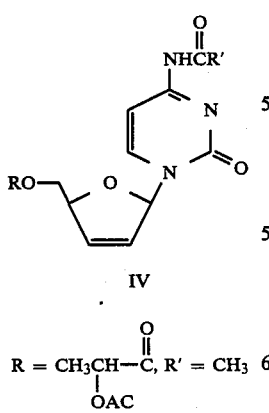

R = CH$_3$CH(OAC)—C(O)—, R' = CH$_3$

A total of 1.47 g of a mixture of bromoacetates from Example 3 was reduced with 800 mg of zinc-copper couple as described in Example 7 to give 570 mg of the product after crystallization from hot tetrahydrofuran, mp 125° C.; $[\alpha]_D^{25}+119.04°$ (c=0.25, CHCl$_3$).

EXAMPLE 9

Preparation of N-Acetyl-2,'3'-didehydro-2',3'-Dideoxycytidine 5'-[2(Acetoxy)Benzoate]

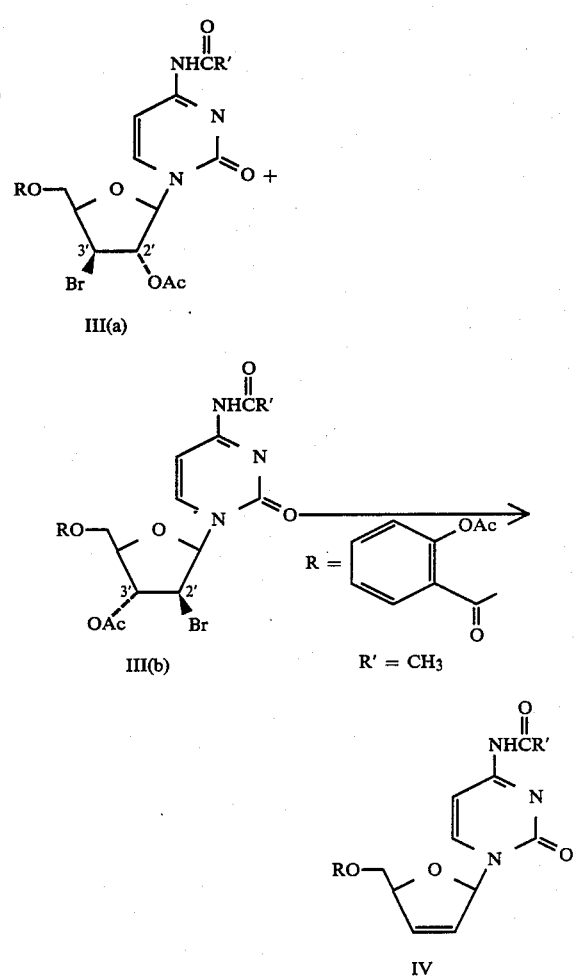

1 1-L, three-necked, round-bottomed flask equipped with a mechanical stirrer and argon inlet was charged with 30.5 g of a mixture of the bromoacetates of Example 4. The mixture was deoxygenated by evacuation followed by filling the reaction vessel with argon; this procedure was repeated twice. 10 g of zinc-copper couple (obtained as in Example 5) was added and the mixture was stirred under argon at room temperature overnight. It was filtered over Celite, and the flask was rinsed out with 20 mL of acetonitrile, and the rinse was used to wash the Celite. The combined filtration and washing were evaporated, and the residue was dissolved in 125 mL of methylene chloride. This was added to a previously prepared solution of 20 g of ethylenediaminetetracetic acid disodium salt dihydrate in 200 mL of water containing 20.0 g of sodium bicarbonate. The mixture was stirred at room temperature for 1.5 h, and filtered over Celite. The organic phase was separated and the aqueous phase was re-extracted with 75 mL of methylene chloride. The combined organic phase was dried (MgSO$_4$) and filtered. The filtrate was treated with 6.0 mL of acetic anhydride and 850 mg of 4-dimethylaminopyridine. The mixture was stirred at room temperature for 2 h, diluted with 25 mL of ethanol, and then concentrated to ca. 100 ml, 25 mL of toluene was added and the mixture was evaporated to dryness. The residue was crystallized from 100 mL of ether-ethanol (1:1) to give 6.3 g of N-acetyl-2′,3′-didehydro-2′,3′-dideoxycytidine 5′-[2(acetoxy)benzoate]. Recrystallization from hot ethanol, tetrahydrofuran (1:1) gave an analytical sample of N-acetyl-2′,3′-didehydro-2′,3′-dideoxycytidine 5′-[2(acetoxy)benzoate], mp 265° C. (dec.), UV (EtOH): 299 (E=9,800), 243 (E=21,550), and 203 (E=48,400) nm.

EXAMPLE 10

Preparation of N-Acetyl 2′,3′-Didehydro-2′,3′-dideoxycytidine 5′-Acetate

To the catholyte reservoir was added 35.0 g (0.081 mol) of 4-(acetylamino)-1-(3′-bromo-2′,5′-di-O-acetyl-β-D-xylofuranosyl-2-(1H)-pyrimidinone III(a)

R′=CH$_3$, and 1.0 L of 0.25M tetraethylammonium tosylate in acetonitrile. To the anolyte reservoir was added 1.0 L of 0.025M tetraethylammonium tosylate in acetonitrile. Both the catholyte and anolyte were circulated through the electrolytic cell at a flow rate of 200 ml/min/cell. The cell was divided by an anion exchange membrane and the initial current density was 2.4 mA/cm$^2$ at −1.5V. The reaction was followed by TLC and HPLC. During the first 8 hr the desired product N-acetyl 2′,3′-dideoxycytidine 5′-acetate started to precipitate from the reaction mixture. The product was removed by filtration and the reaction continued. After 16 hr, this reaction was almost complete. The catholyte mixture was collected and evaporated to dryness at room temperature and 10 mm vacuum. The dried residue was combined with the previously filtered solids. The mixture of product and electrolyte was then dissolved in 200 mL of deionized water. The mixture was extracted with 3×300 ml=900 of methylene chloride. The organic extract was dried over anhydrous sodium sulfate and evaporated to dryness. The residue was triturated with 180 ml of tetrahydrofuran to give 18.12 g (76% yield) of N-acetyl 2′,3′-didehydro-2′,3′-dideoxycytidine 5′-acetate, IV,

R′=CH$_3$, m.p.>300° (dec); $[\alpha]_D^{25}$+14.7° (c=0.387, DMSO). The product was analyzed by HPLC to give a 99.2% assay.

EXAMPLE 11

Preparation of N-Acetyl 2′,3′-Didehydro-2′,3′-dideoxycytidine 5′-isobutylacetate To the catholyte reservoir was added 10.0 g (0.019 mol) of 1-(3-bromo-3-deoxy-2-O-acetyl-5O-α-acetoxyisobutyrl-β-D-xylofuranosyl)-N$^4$-acetylcytosine and 500 mL of 0.25M tetraethylammonium tosylate in acetonitrile. To the anolyte reservoir was added 500 mL of 0.025M tetraethylammonium tosylate in acetonitrile. Both the catholyte and anolyte were circulated through the electrolytic cell at a flow rate of 250 ml/min/cell. The cell was divided by an anion exchange membrane (Ionac MA-3475, Sybron Chemical Division, Birmingham, NJ) and the initial current density was 0.8 mA/cm$^2$ at −4.0V. The reaction was monitored by TLC and HPLC. During the first 30 minutes, a sample analyzed gave 60% conversion. About 90 minutes later, the TLC sample showed total disappearance of the starting material. The alkene products were identified by HPLC as a mixture of products. The catholyte solution was collected and evaporated to dryness at room temperature in vacuo. The dried residue was then dissolved in 200 mL of deionized water. The solution was extracted with 3×200 ml=600 of methylene chloride (Fisher). The organic extract was dried over anhydrous sodium sulfate and was then evaporated to dryness to yield 3.07 g of tan-colored solids (yield, 42%). A total of 0.5 g of the product mixture was dissolved in 8 mL of hot tetrahydrofuran and allowed to stand overnight to effect crystallization. The solid crystalline mass was filtered and washed with 10 mL of ether to give 0.22 g of N-acetyl 2′,3′-didehydro-2′,3′-dideoxycytidine 5′-isobutyrlacetate. Recrystallization from hot tetrahydrofuran gave crystals m.p. 170°–172° C.

EXAMPLE 12

Preparation of N-Acetyl 2′,3′-Dideoxycytidine 5′-Acetate

In a 50 L flask fitted with a hydrogen inlet tube and an argon inlet tube was placed 16.0 L of tetrahydrofuran and 22.0 L of methanol, followed by a slurry of 500.0 g (1.71 moles) of N-acetyl 2′,3′-didehydro-2′,3′-dideoxycytidine 5′-acetate in 1.5 L of methanol. Then any solid starting material was washed from the glassware into the flask with an additional 500 mL of methanol. With the mixture layered with argon, 20.0 g of 10% palladium on carbon catalyst in 200 mL of methanol was carefully added. The flask was then evacuated (70 mm) and layered with hydrogen gas. The evacuation-layering process was carried out three times. A hydrogen pressure of 1 atmosphere was then maintained as the mixture was stirred at room temperature. After 52 minutes the reaction slowed markedly and a sample was removed for HPLC analysis to trace the disappearance of starting material. The flask was evacuated (70 mm) and layered with argon gas. This evacuation-layering process was carried out three times. The reaction mixture was then cautiously filtered through a 1′ Celite pad. The pad was then washed with 500 mL of ca. 40% tetrahydrofuran in methanol. The filtration was then concentrated to dryness at 50° (70 mm) on a large rotary evaporator. In the same manner 9×500.0 g=4.50 (15.39 moles) of olefin 5 was hydrogenated to a mixture of N-acetyl 2′,3′-dideoxycytidine 5′-acetate and a small amount of N-acetylcytosine by-product. The filtrate was concentrated at 70–80% (70 mm) on a large rotary evaporator or give a white to off-white solid. The solid was triturated with 4.5 L of acetonitrile, by stirring the solid for 15 minutes. The paste was cooled to 10° for 15 minutes and filtered to remove acetonitrile soluble impurities [small amounts of overhydrogenated products such as 5,6-dihydro-2′,3′-dideoxyuridine 5′-acetate. The white filter cake was then dissolved in 200 of hot acetonitrile to give a cloudy solution. This solution was filtered through a 1″ pad of Celite to remove insoluble N-acetylcytosine. The colorless filtrate was concentrated at 70°–80° (70 mm) to a 10 L volume and the recovered acetonitrile was saved for recycling. The concentrated solution was chilled to 10° for 1 hr to induce crystallization. The solid was collected on a Büchner funnel and washed with 2×2.0=4.0 L of cold acetonitrile. The white solid was dried at 80° in a steam oven to yield 3.30 kg (66%) of first crop N-acetyl 2′,3′-dideoxycytidine 5′-acetate, m.p. 210°–211°, $[\alpha]+92.0°$ (c 0.49, $CH_3OH$).

The mother liquors and washes were pooled from several runs and concentrated. Recrystallization of this material yielded an additional 10–16% of N-acetyl 2′,3′-dideoxycytidine 5′-acetate of comparable quality. The mother liquors from this second crop material contained small amounts of the 5,6-dihydro-2′,3′-dideoxyuridine 5′-acetate. Purification of these mother liquors on 70–230 mesh silica gel 60 with 10:1 ethyl acetate-methanol gave an additional 3–5% of desired product.

EXAMPLE 13

Preparation of a mixture of N-acetyl 2′,3′-Dideoxycytidine 5′-acetate and N-acetyl 2′,3′-Dideoxycytidine-5′-isobutrylacetate

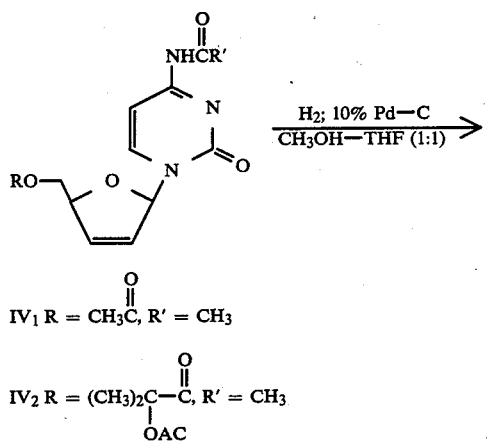

A 5 L three-necked, round-bottomed flask (creased) equipped with a mechanical stirrer was charged with a mixture of 142.3 g of the bromoacetates from Example 7 in 800 mL of methanol. The mixture was warmed until a solution was obtained, diluted with 800 mL of tetrahydrofuran, and then cooled to room temperature. A total of 8.9 g of 10% palladium on charcoal was added under argon and the mixture was hydrogenated with stirring at room temperature and atmospheric pressure until hydrogen uptake ceased (11 L, ca. 3 hr). The mixture was filtered over Celite and the Celite was washed with 300 mL of methanol. The combined filtrate and washing were evaporated to give 132.7 g of a mixture of products as a somewhat hydroscopic foam.

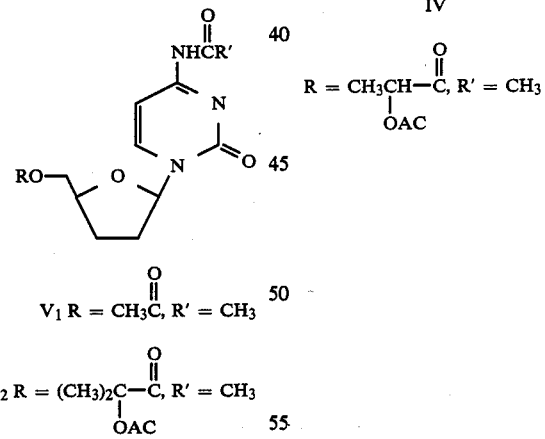

| Compound | Percent | Relative Retention Time RRT (min) |
|---|---|---|
| $V_1$ R = $CH_3\overset{O}{\overset{\|}{C}}$, R′ = $CH_3$ | 6% | 7.40 |
| $V_2$ R = $(CH_3)_2-\underset{OAC}{\overset{}{C}}-\overset{O}{\overset{\|}{C}}-$, R′ = $CH_3$ | 90% | 17.93 |
| N—Acetylcytosine | 1% | 3.67 |

A pure sample of N-acetyl 2′,3′-dideoxycytidine 5′-isobutylacetate was obtained as a foam by chromatography over silica gel with 1 percent methanol in methylene chloride, $[\alpha]_D^{25}+136.08$ ($CHCl_3$) C=1.02.

EXAMPLE 14

Preparation of [2R-[2 alpha, 5 alpha (S*)]]-N-[1-[5-[[2-(Acetyloxy)-1-oxopropoxy]methyl]-tetrahydro-2-furanyl]-1,2-dihydro-2-oxo-4-pyrimidinyl]acetamide

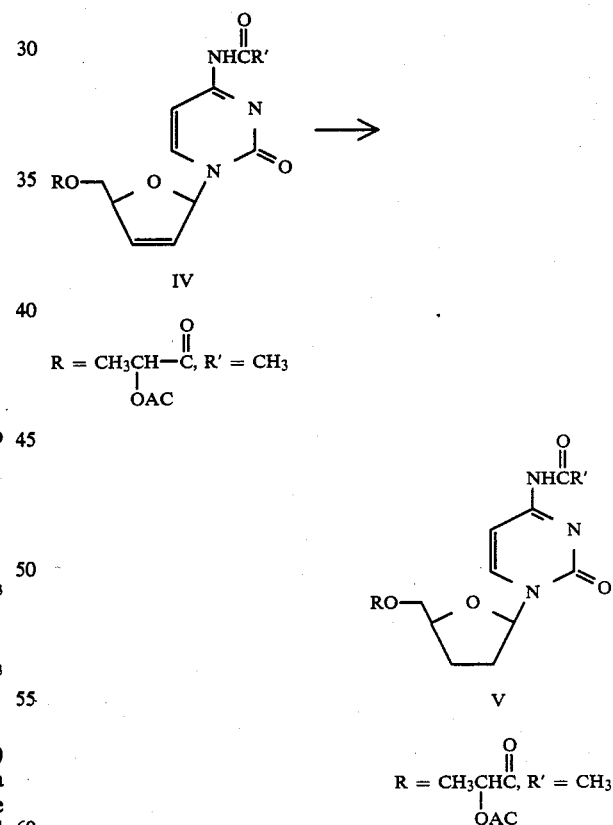

A solution of 720 mg of the alkene from Example 8 set forth in 10 mL of methanol and 10 mL of tetrahydrofuran was hydrogenated over 200 mg of 10% palladium on charcoal at room temperature and atmospheric pressure until hydrogen uptake ceased (10 ml). The mixture was filtered over Celite and the filtrate was evaporated to give a gum. Chromatography on 10 g of silica (70–230 mesh) with 10% methanol in methylene chloride, gave 290 mg of the product as a foam, $[\alpha]_D^{25}+88.43$ (C=0.99, CHCl$_3$); UV (EtOH): 299 (E=6,420), 246 (E=1241°), and 214 (E=16,500, nm).

EXAMPLE 15

Preparation of 2′,3′-Dideoxycytidine

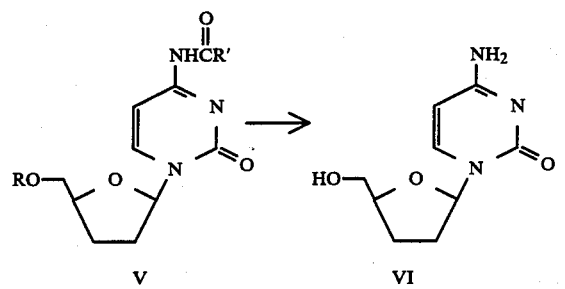

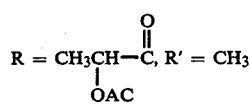

A solution of 20.7 g of the product from Example 14 in 100 mL of ethanol was treated with 10.0 mL of Triton B (N-benzyltrimethyl-ammonium hydroxide), and the mixture was stirred at room temperature overnight. The mixture was concentrated to 20 ml, cooled to 0° C., and the product was collected by filtration. It was washed with 10 mL of cold ethanol to give 4.48 g of 2′,3′-dideoxycytidine, mp 215°–218° C., as an off-white solid.

EXAMPLE 16

Preparation of N-Acetyl-2,′3′-Dideoxycytidine 5′-[2(Acetoxy)Benzoate]

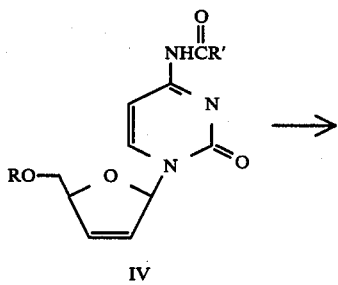

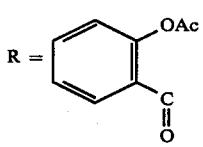

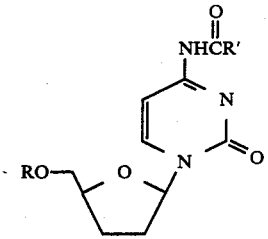

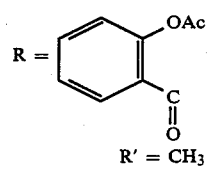

A 250-ml, round-bottomed flask was charged with 1.66 g of the product of Example 9 in 30 mL of methanol and 30 ml of dimethylformamide. A total of 300 mg of 10% palladium on charcoal was added under argon and the mixture was hydrogenated with stirring at room temperature and atmospheric pressure until hydrogen uptake ceased (113 ml). The mixture was filtered over Celite and the filtrate was evaporated in vacuo to give a gum, which was chromatographed on 15 g of silica gel with 2% methanol in methylene chloride as eluent to give 970 mg of the product as a white foam; UV (EtOH); 298 (E=9.450) 243 (E=19,500), and 203 (E=42,350) nm.

EXAMPLE 17

Preparation of 2′,3′-Didexoycytidine

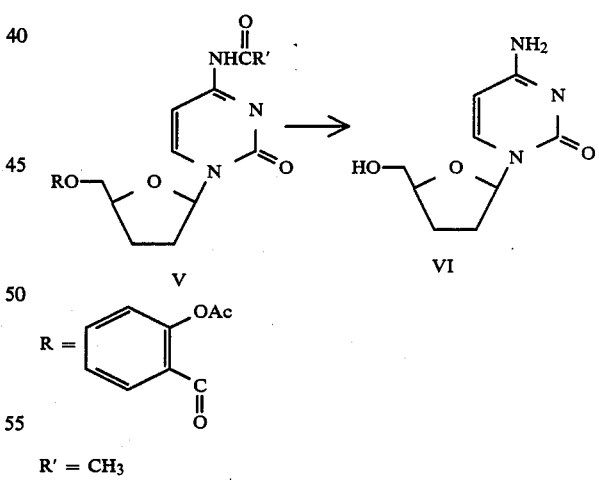

A solution 1-L, three-necked, round-bottomed flask equipped with a mechanical stirrer was charged with 33.4 g of the product of Example 16 in 330 mL of methanol, 33 mL of water, and 66 mL of triethylamine. The mixture was stirred, under argon, at 65° C. for 7 h, and then at room temperature overnight. It was concentrated in vacuo and the residue was azeotroped three times with toluene. The residue was dissolved in 50 mL of ethanol, and diluted with 400 mL of acetone, and stirred at room temperature overnight. The product was collected by filtration to give 4.04 g of 2',3'-didexoycytidine, m.p. 218°–220° C.

EXAMPLE 18

Preparation of 2',3'Dideoxycytidine

A 22.0 L three-necked, round-bottomed flask equipped with mechanical stirrer, a thermometer and a condenser was placed in a large heating bath and charged with 1.55 kg (5.25 moles) of N-acetyl 2',3'-dideoxycytidine 5'-acetate 10.6 L of methanol, 3.1 L of triethylamine, and 1.56 L of deionized water. The heating bath was filled with hot water and the temperature was raised to 60°–65°. The flask contents were stirred at 55°–60° for 3 hr, then at ambient temperature for 12. The reaction mixture was concentrated in vacuo at 70°–80° (70 mm) on a large rotary evaporator to a volume of 2.5 L to induce crystallization. To the white semi-solid was added 1.5 L of absolute ethanol and again the mixture was concentrated in vacuo to 2.5 L volume to remove residual solvents. The white semi-solid was cooled to 10° C. for 0.5 hr and was collected by filtration and washed with 1.5 L of absolute ethanol. The damp white solid was recrystallized from 50.0 L of absolute ethanol at reflux and filtered through a sintered glass funnel to remove any particulate matter. The filtrate was concentrated in vacuo at 70°–80° (70 mm) on a rotary evaporator to a volume of 3.0 L. The semi-solid was then heated for 10 minutes without vacuum at reflux in the rotary evaporator. The mixture was cooled to 10° C. for 2 hr to effect crystallization and the white solid was collected by filtration, and washed with 2×1.0 L=2.0 L of absolute ethanol. The solid was dried in a vacuum oven at 85° C. and 1 mm overnight to yield 1.02 kg (92%) of 2',3'-dideoxycytidine as a white solid, m.p. 225°–228° C; $[\alpha]_S^{25}+76.9°$ (c 0.56, H$_2$O); $[\alpha]_D^{25}+105.0°$ (c 0.50, CH$_3$OH); lit. m.p. 215°–217°; $[\alpha]_D^{25}+81°$ (c 0.635, H$_2$O) [J. P. Horowitz, J. Chua, M. Noel, and J. T. Donatti, *J. Org. Chem.*, 32, 817 (1967)]. The mother liquors from three batches were pooled and concentrated to a volume of 1.0 L to effect recrystallization. This solid was recrystallized from 5.0 L of absolute ethanol which was concentrated to a volume of 1.0 L to yield 2–4% additional 2',3'-dideoxycytidine. The second crop mother liquors were combined and purified by column chromatography on 70–230 mesh silica gel 60 using 65:1 methylene chloride-methanol-water as eluant. In this manner, cytosine, 5,6-dihydro-2',3'-deoxyuridine and 5,6-dihydrouracil were also isolated and characterized.

EXAMPLE 19

Preparation of 2',3'-Didexoycytidine

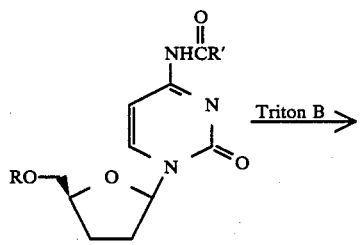

-continued

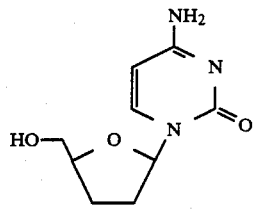

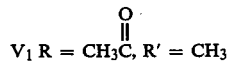

V$_1$ R = CH$_3$C, R' = CH$_3$

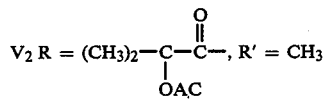

V$_2$ R = (CH$_3$)$_2$—C—C—, R' = CH$_3$
           |
          OAC

A 250 mL three-necked, round-bottomed flasks equipped with a stirrer and an argon inlet tube was charged with 27.2 g of the mixture of the compounds from Example 13 in 71.0 mL of methanol. The mixture was stirred at room temperature until a solution was stirred at room temperature until a solution was obtained (this takes a few minutes) and then treated with 7.14 mL of Triton B (40% Benzyltrimethyl-ammonium hydroxide in methanol). Stirring was continued at room temperature overnight and the product was collected by filtration. It was washed with some cold methanol to give 8.33 g of crude 2',3'-didexoycytidine, with a purity of 99.17% (HPLC). Evaporation of the filtrate and washing gave a semisolid to which 20.0 mL of ethanol was added. The product was collected by filtration, washed with some cold ethanol, to give an additional 1.05 g of crude (96.67% by HPLC) 2',3'-didexoycytidine, a total of 9.38 g of crude 2',3'-didexoycytidine (43.1% from N-acetylcytidine).

Crystallization.

The combined crude 2',3'-didexoycytidine above (9.38 g) was dissolved in a mixture of 100 mL of hot (reflux) absolute ethanol and 12 mL of deionized water. The hot solution was filtered, and the funnel was washed with 10 mL of ethanol. The combined filtrate and washing were allowed to cool to room temperature and cooled further to ca. 7° C. (ice-bath). The product was collected by filtration and washed with a few mL of ethanol to give 7.17 g of 2',3'-didexoycytidine, as white crystals, m.p. 219°–221° C., $[\alpha]_D^{25}+95.86°$ (CH$_3$OH, c=1.46).

While the invention has been described in connection with the preferred embodiment, it is not intended to limit the scope of the invention to the particular form set forth, but, on the contrary, it is intended to cover such alternatives, modifications and equivalents as may be included within the spirit and scope of the appended claims.

We claim:

1. A compound of the formula:

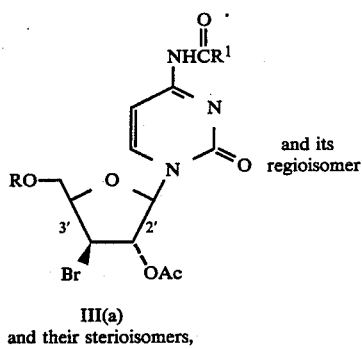

III(a)
and their sterioisomers,

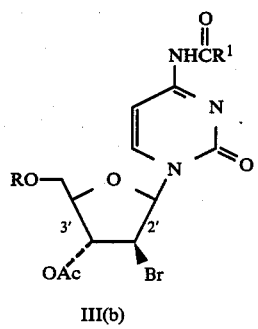

III(b)

wherein R' is substituted or unsubstituted lower alkyl, aryl, or aralkyl with the substituents selected from the group consisting of halogen, alkyl, nitro, or alkoxy; and R is substituted or unsubstituted 2-acetoxy-2-methylpropanoyl, 2-acetoxypropanoyl, or 2-acetoxybenzoyl with the substituents selected from the group consisting of lower alkyl, aryl, or aralkyl.

2. The compound of claim 1 wherein R' is lower alkyl.

3. The compound of claim 2 wherein R' is CH$_3$.

4. The compound of claim 3 wherein R is selected from the group consisting of unsubstituted 2-acetoxy-2-methylpropanoyl, 2-acetoxypropanoyl, or 2-acetoxybenzoyl.

5. The compound of claim 4 wherein R is 2-acetoxy-2-methylpropanoyl.

6. the compound of claim 4 wherein R is 2-acetoxypropanoyl.

7. The compound of claim 4 wherein R is 2-acetoxybenzoyl.

8. A compound of the formula:

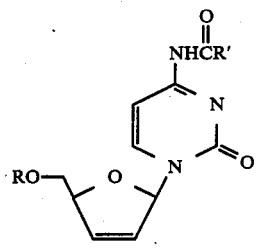

wherein R' and R are as in claim 1.

9. The compound of claim 8 wherein R' is lower alkyl.

10. The compound of claim 9 wherein R' is CH$_3$.

11. The compound of claim 10 wherein R is selected from the group consisting of unsubstituted 2-acetoxy-2-methylpropanoyl, 2-acetoxypropanoyl, or 2-acetoxybenzoyl.

12. The compound of claim 11 wherein R is 2-acetoxy-2-methylpropanoyl.

13. The compound of claim 11 wherein R is 2-acetoxypropanoyl.

14. The compound of claim 11 wherein R is 2-acetoxybenzoyl.

15. A compound of the formula:

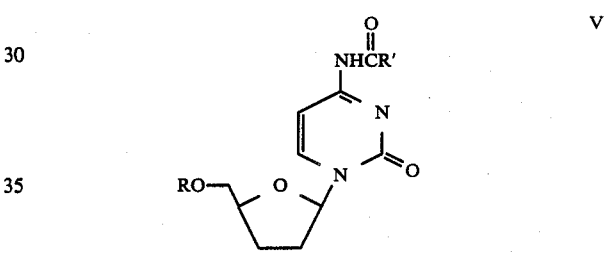

wherein R' and R are as in claim 1.

16. The compound of claim 15 wherein R' is lower alkyl.

17. The compound of claim 16 wherein R' is CH$_3$.

18. The compound of claim 17 wherein R is selected from the group consisting of unsubstituted 2-acetoxy-2-methylpropanoyl, 2-acetoxypropanoyl, or 2-acetoxybenzoyl.

19. The compound of claim 18 wherein R is 2-acetoxy-2-methylpropanoyl.

20. The compound of claim 18 wherein R is 2-acetoxypropanoyl.

21. The compound of claim 20 wherein R is 2-acetoxybenzoyl.

* * * * *